United States Patent [19]
Galle

[11] Patent Number: 5,993,806
[45] Date of Patent: Nov. 30, 1999

[54] METHOD OF STABILIZING PHARMACEUTICAL PREPARATIONS COMPRISING DIGESTIVE ENZYME MIXTURES

[75] Inventor: Manfred Galle, Isernhagen, Germany

[73] Assignee: Solvay Pharmaceuticals GmbH, Hannover, Germany

[21] Appl. No.: 08/916,325

[22] Filed: Aug. 22, 1997

[30] Foreign Application Priority Data

Aug. 28, 1996 [DE] Germany ............................ 196 34 752
Jun. 12, 1997 [DE] Germany ............................ 197 24 845

[51] Int. Cl.⁶ .......................... A61K 38/54; A61K 35/39; A61K 35/37; A61F 2/00
[52] U.S. Cl. ................... 424/94.3; 424/94.2; 424/94.21; 424/428; 424/550; 424/556
[58] Field of Search .............................. 424/94.2, 94.21, 424/94.3, 428, 435, 550, 556

[56] References Cited

U.S. PATENT DOCUMENTS

| | | | |
|---|---|---|---|
| 3,956,483 | 5/1976 | Lewis | 424/94.21 |
| 3,991,180 | 11/1976 | Boettner et al. | 424/94.3 |
| 4,019,958 | 4/1977 | Hell et al. | 435/186 |
| 4,242,219 | 12/1980 | Bogerman et al. | 510/392 |

FOREIGN PATENT DOCUMENTS

| | | |
|---|---|---|
| 42 00 002 | 7/1993 | Germany . |
| 59-169491 | 9/1984 | Japan . |
| 2029950 | 2/1987 | Japan . |
| 9-125096 | 5/1997 | Japan . |
| WO 91/14454 | 10/1991 | WIPO . |
| WO 95/07688 | 3/1995 | WIPO . |

OTHER PUBLICATIONS

DeRobertis. Cell and Molecular Biology, 7th ed. pp. 132–133, 1980.

Chemical Abstracts, No. 99: 200535j entitled "Capsules Containing Stable Digestive Enzymes", vol. 99 (1983) p. 342.

Primary Examiner—Leon B. Lankford, Jr.
Assistant Examiner—Christopher R. Tate
Attorney, Agent, or Firm—Evenson, McKeown, Edwards & Lenahan, P.L.L.C.

[57] ABSTRACT

The use of complex lipids, especially lecithin, as additives to stabilize water-soluble pharmaceutical preparations of digestive enzyme mixtures containing lipases and proteases, especially pancreatin-containing digestive enzyme mixtures, which are suitable for preparing aqueous solutions for continuous introduction into the gastrointestinal tract by means of a tube, against a decrease in lipolytic activity under the influence of moisture.

33 Claims, No Drawings

METHOD OF STABILIZING PHARMACEUTICAL PREPARATIONS COMPRISING DIGESTIVE ENZYME MIXTURES

BACKGROUND OF THE INVENTION

The present invention relates to the use of complex lipids as additives stabilizing against a decrease in lipolytic activity under the influence of moisture to water-soluble pharmaceutical preparations of digestive enzyme mixtures which contain protease/lipase mixtures, in particular pancreatin, and which are suitable for preparing aqueous solutions for continuous introduction into the gastrointestinal tract by means of tubes. The invention furthermore relates to water-soluble pharmaceutical preparations of digestive enzyme mixtures containing lipases and proteases, especially of pancreatin-containing digestive enzyme mixtures, which are stabilized by complex lipids against a decrease in lipolytic activity under the influence of moisture, and which are suitable for preparing aqueous solutions which can be introduced into the gastrointestinal tract of mammals or humans by means of a tube.

A deficiency of digestive enzymes may occur in mammals, especially humans, for example caused by a pathological change in the pancreas resulting from chronic pancreatitis, digestive insufficiency after stomach operations, hepatic or biliary disorders. It is already known that deficiency manifestations of these types can be treated by administration of non-endogenous pancreatin-containing digestive enzyme mixtures such as, for example, pancreatic enzymes, especially pancreatin, which may optionally also contain added lipases. The pancreatic enzymes are normally administered orally in the form of solid preparations. In order for the administered enzyme mixtures taken orally not to undergo unwanted irreversible denaturation in the stomach by gastric acid and proteolytic enzymes, such as pepsin, present therein, it is necessary to provide the enzyme mixtures with a coating resistant to gastric fluid. A coating of this type permits the intact enzyme mixtures to pass through the stomach to their site of action, the duodenum, where the protective layer is degraded by the neutral to slightly alkaline conditions prevailing therein, and the enzymes are released. Like the endogenous pancreatic enzymes of the healthy person, the orally administered enzymes are able to display their enzymatic effects, in particular amylolytic, lipolytic and proteolytic activities, there.

Solid pancreatin formulations of this type which can be coated with a film resistant to gastric fluid and are in the form of micropellets are described, for example, in Bodecker et al., U.S. Pat. No. 5,378,462 (=DE 4,227,385), the disclosure of which is incorporated herein by reference.

For patients with digestive insufficiency, in particular patients confined to bed with prolonged digestive insufficiency such as, for example, chronic pancreatic insufficiency, it would be desirable to administer non-endogenous digestive enzymes also over a lengthy period in liquid form, for example by continuous administration by means of a tube, in place of solid dosage forms.

It has not heretofore been possible to provide liquid dosage forms of pancreatin-containing digestive enzyme mixtures, in particular of pancreatin, because liquid aqueous preparations of such enzyme mixtures are not stable over a lengthy period. It has been found, in particular, that the activity of the lipases present in the mixture decreases rapidly in the presence of water due to proteolytic attack by the proteases which are likewise present in the mixture, such as trypsin or chymotrypsin. Thus, there may be substantial loss of lipase activity in aqueous pancreatin preparations within a very short time depending on the external conditions (temperature, pH).

In order to be suitable for continuous introduction into the gastrointestinal tract by administration by means of a tube, aqueous solutions of digestive enzyme mixtures containing lipases and proteases, in particular of pancreatin-containing digestive enzyme mixtures, must be stable for a period of several hours, for example 8 hours. In particular, no particles blocking the tube must be produced or present in the solutions. An essential requirement for solutions of this type is that an activity of all the digestive enzymes present therein which is as high and as constant as possible is maintained throughout the administration period. It is furthermore necessary for solutions suitable for continuous gastrointestinal administration that they are free of microbe growth, that is to say can be provided for example preserved against microbe growth, preferably sterile.

SUMMARY OF THE INVENTION

It was therefore an aim of the invention to provide water-soluble pharmaceutical preparations of digestive enzyme mixtures which contain lipases and proteases, are stabilized against loss of lipolytic activity under the influence of moisture, and remain stable dissolved in aqueous medium over an extended period of time.

These and other aims of the invention have been achieved by providing a method of stabilizing a water-soluble pharmaceutical preparation comprising a lypolytic mixture of digestive enzymes selected from the group consisting of lipases and proteases, against a decrease in lipolytic activity under the influence of moisture, the pharmaceutical preparation being suitable for preparing an aqueous solution for continuous introduction through a tube into the gastrointestinal tract of a patient, the method comprising incorporating into the pharmaceutical preparation an effective lypolytic activity stabilizing amount of at least one complex lipid additive.

In accordance with another aspect of the invention, the aims have been realized by providing a water-soluble pharmaceutical preparation suitable for preparing an aqueous solution for continuous introduction through a tube into the gastrointestinal tract of a patient, the pharmaceutical preparation comprising a mixture of digestive enzymes selected from lipases and proteases, and further comprising an amount of at least one complex lipid sufficient to stabilize the digestive enzyme mixture against a decrease in lipolytic activity under the influence of moisture.

In yet another preferred aspect of the invention, the aims are achieved by providing a kit for preparing an aqueous solution of a digestive enzyme mixture suitable for continuous introduction through a tube into the gastrointestinal tract of a patient, said digestive enzyme mixture being stabilized against a decrease in lipolytic activity and free of microbe growth, the kit comprising (a) a water-soluble, solid pharmaceutical preparation comprising a mixture of digestive enzymes selected from lipases and proteases, said preparation being free of microbe growth; and (b) an amount of an aqueous solvent sufficient for preparing the aqueous solution, said solvent being free of microbe growth; and the kit further comprising an amount of at least one complex lipid contained in the pharmaceutical preparation and/or the aqueous solvent, the amount of the complex lipid being sufficient to stabilize the aqueous solution, which is to be prepared, against a decrease in lypolytic activity.

DETAILED DESCRIPTION OF PREFERRED EMBODIMENTS

The invention relates to the use of complex lipids as additives stabilizing against a decrease in lipolytic activity under the influence of moisture in water-soluble pharmaceutical preparations of digestive enzyme mixtures which contain lipases and proteases, in particular pancreatin-containing digestive enzyme mixtures, and which are suitable for preparing aqueous solutions for continuous introduction into the gastrointestinal tract by means of a tube. The invention furthermore relates to water-soluble pharmaceutical preparations of digestive enzyme mixtures which are stabilized in this way. The invention likewise relates to kits for preparing aqueous solutions of digestive enzyme mixtures suitable for continuous administration by tube.

Complex lipids which are suitable according to the invention as stabilizing additives are, as a rule, insoluble in acetone. These include, in particular, the phosphorus-containing and carbohydrate-free phospholipids, and the carbohydrate-containing and non-phosphorus-containing glycolipids and mixtures thereof. It is expedient to use only phospholipids or mixtures containing phospholipids and glycolipids.

Suitable phospholipids which can be used according to the invention as stabilizing additives to digestive enzyme mixtures containing lipases and proteases, especially pancreatin-containing digestive enzyme mixtures, are, in particular, salts of anions of the general formula I

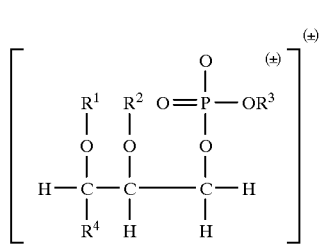

in which
- $R^1$ denotes hydrogen or an alkanoyl radical with 10–25 carbon atoms, whose hydrocarbon radical may optionally contain 1–4 double bonds,
- $R^2$ denotes hydrogen or an alkanoyl radical with 10–25 carbon atoms, whose carbon radical may optionally contain 1–4 double bonds, or, if $R^1$ does not represent hydrogen, can also denote hydrogen,
- $R^3$ denotes hydrogen, a lower alkyl group which can be substituted by amino, lower trialkylammonium, a carboxyl group bonded to a carbon atom carrying an amino functionality, or a hydroxyl-substituted cycloalkyl group,
- $R^4$ denotes hydrogen or a hydrocarbon chain with 10–25 carbon atoms, which may optionally contain 1–4 double bonds,
- A represents oxygen or NH, with a physiologically acceptable cation.

Suitable physiologically acceptable cations include ammonium ions, alkali metal or alkaline earth metal cations, preferably sodium, potassium or calcium, and other physiologically acceptable singly or multiply charged cations. When $R^3$ contains a nitrogen atom, this can form a quaternary ammonium ion which can likewise serve as cation, so that inner salts with no external charge are formed.

When the radicals $R^1$ and/or $R^2$ in the compounds of the formula I represent an alkanoyl radical, this can be straight-chain or branched and is, as a rule, unbranched and contains 10–25, preferably 16–20, carbon atoms. The alkanoyl radical may optionally contain up to four double bonds. Alkanoyl radicals which may be present are, in particular, radicals of long-chain fatty acids such as nervonic acid, lignoceric acid, palmitic acid, palmitoleic acid, stearic acid, oleic acid, linoleic acid, linolenic acid, arachidic acid or arachidonic acid.

Where the substituent $R^3$ denotes or contains a lower alkyl group, this can be straight-chain or branched and contain, in particular, 1 to 4, preferably 1 to 2, carbon atoms. Where $R^3$ denotes a hydroxyl-substituted cycloalkyl group, this can contain 3 to 6 carbon atoms and be substituted one or more times by hydroxyl. The cycloalkyl group preferably contains 5 to 6 carbon atoms, each of which may be substituted by hydroxyl.

The $R^3O$ group preferably represents hydroxyl or an alkoxy radical which has been produced by esterifying a mono- or polyhydric alcohol with the phosphate group, the mono- or polyhydric alcohol being selected from the group consisting of aminoethanol, choline, serine, glycerol and myoinositol.

Where the radical $R^4$ represents a hydrocarbon chain, this can be straight-chain or branched and is, as a rule, unbranched and contains 10–25, preferably 12–20, particularly preferably 15, carbon atoms. The hydrocarbon chain can optionally contain up to 4, preferably 2, particularly preferably 1, double bond.

The radical A can represent oxygen or the NH group.

Suitable and preferred phospholipids include, for example, phosphatidic acid (1,2-diacyl-sn-glycerol-3-phosphoric acid), phosphatidylcholine(1,2-diacyl-sn-glycerol-3-phosphorylcholine), phosphatidylethanolamine (1,2-diacyl-sn-glycerol-3-phosphorylethanolamine), phosphatidylserine(1,2-diacyl-sn-glycerol-3-phosphorylserine) and phosphatidylinositol(1,2-diacyl-sn-glycerol-3-phosphorylinositol) and, in the case where the phospholipids derive from animal sources of origin such as, for example, chicken egg, also sphingomyelin, and mixtures of these compounds. The said 1,2-diacylphospholipids may be partially hydrolysed under certain conditions, for example the enzymatic effect of a phospholipase. Depending on the nature of the phospholipase, in this case the radicals $R^1$, $R^2$, $R^3$ or else $[R^3OPO_2]^-$ in the 1,2-diacylphospholipids may be replaced by hydrogen. If at least one of the said molecular radicals in each phospholipid molecule is hydrolysed, then so-called lysophospholipids are produced, in particular lysophosphatidylcholine, lysophosphatidylethanolamine, lysophosphatidylinositol, lysophosphatidylserine and lysophosphatidic acid. These lysophospholipids are also suitable as stabilizing additives to digestive enzyme mixtures containing lipases and proteases, in particular pancreatin-containing digestive enzyme mixtures, for the purpose of the invention.

Glycolipids which can be used in particular are so-called phytoglycolipids, which occur in plants, of the general formula II

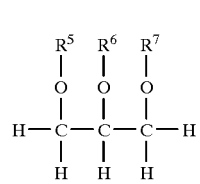

in which
- $R^5$ and $R^6$ each, independently of one another, designate an alkanoyl radical with 10–25 carbon atoms, whose hydrocarbon radical may optionally contain 1–4 double bonds, or denotes hydrogen, but where $R^5$ and $R^6$ cannot both denote hydrogen, and
- $R^7$ denotes a mono- or disaccharide residue whose saccharide units are selected from the group consisting of D-fructosyl, D-galactosyl, D-glucosyl and D-mannosyl and mixtures thereof.

Where $R^5$ and $R^6$ in the compounds of the formula II represent an alkanoyl radical, this is branched or unbranched and is, as a rule, unbranched and contains 10–25, preferably 16–20, carbon atoms. The alkanoyl radical may optionally contain up to 4 double bonds. Radicals of long-chain fatty acids such as palmitic acid, palmitoleic acid, stearic acid, oleic acid, linoleic acid, linolenic acid or arachidic acid are particularly suitable as alkanoyl radicals.

The $R^7$ radicals represent mono- or disaccharide residues which may be composed of the sugar molecules D-galactose, D-glucose, D-mannose or D-fructose. The particularly preferred meaning of $R^7$ is D-galactose (then the compounds are monogalactosyl-diglycerides, MGDG) or digalactose (then the compounds are digalactosyldiglycerides, DGDG; 1,2-diacyl-[α-D-galactosyl-(1→6)-β-D-galactosyl-(1→3)]-sn-glycerols).

The phospholipids of the general formula I and the glycolipids of the general formula II each have an asymmetric center or center of chirality on the middle carbon atom in the glycerol basic structure and may have the R or S configuration. It is possible for the purpose of the invention to use the individual stereoisomeric forms of the compounds of the formula I and/or of the formula II, and the corresponding mixtures.

The lipid mixtures which have proved beneficial for the stabilization according to the invention of the pharmaceutical preparations of digestive enzyme mixtures containing lipases and proteases, in particular pancreatin-containing digestive enzyme mixtures, are those which can be obtained from natural sources and which represent mixtures of various phospholipids and, where appropriate, various glycolipids. Lecithins may be mentioned as preferred examples of such natural lipid mixtures. Sources of such natural lecithins may be, in particular, plants such as soya beans, sunflowers, rapeseed, maize or peanuts and animals or animal products such as egg yolk or cerebral matter, but also microorganisms. Lecithins of natural origin are generally commercially available from various suppliers.

Particularly suitable for the purpose of the invention among the lecithins obtained from plants is soya lecithin, especially soya lecithin enriched in phospholipids, such as, for example, soya lecithin with a content of about 98% of phospholipids. Untreated, non-enriched plant lecithins as a rule contain a certain proportion of phytoglycolipids. Lecithins obtained naturally are mixtures of various phospholipids and, in the case of a plant origin, also glycolipids, whose composition is not uniform, but may vary depending on their origin. Thus, besides the constituents already mentioned above, other phospholipids may also be present in minor amounts. Table 1 serves to illustrate the average compositions of some untreated, non-enriched commercially available lecithins of natural origin.

TABLE 1

Composition of some lecithins (%)

| | Soya lecithin | Rapeseed lecithin | Peanut lecithin | Egg lecithin |
|---|---|---|---|---|
| Phosphatidylcholine | 22 | 37 | 23 | 73 |
| Phosphatidylethanolamine | 23 | 29 | 8 | 17 |
| Phosphatidylserine | 2 | — | — | — |
| Phosphatidylinositol | 20 | 14 | 17 | 1 |
| Phosphatidic acid | 5 | — | 2 | — |
| Sphingomyelin | — | — | — | 3 |
| Phytoglycolipids | 13 | 20 | 38 | 0 |
| Other phospholipids | 12 | — | 12 | — |

The pharmaceutical preparations stabilized according to the invention preferably contain pancreatin-containing digestive enzyme mixtures.

For the purpose of the present invention, pancreatin means pancreatin which has been isolated from mammalian pancreas and whose content of active proteases has optionally been increased by autolytic cleavage of the protease zymogens originally present therein.

It is possible and preferred for the pancreatin-containing digestive enzyme mixtures in the pharmaceutical preparations stabilized according to the invention to comprise pancreatin obtained from mammalian pancreas, in particular porcine pancreatin, which represents a mixture of various digestive enzymes. Mammalian pancreatin suitable as an aid to digestion for the human diet, in particular pancreatin from pig pancreas, does not always contain lipases in sufficient amounts for human needs. It is therefore possible to add to such pancreatin products additional lipase, for example obtained from microorganisms. The pancreatin/lipase mixtures obtained in this way also represent suitable enzyme mixtures.

The proteases in pancreatin isolated from mammals are, if the pancreatin has not been subjected to further pretreatment, normally mostly in the form of a proteolytically inactive precursor, the zymogens. It may therefore be expedient for pharmaceutical purposes to subject the crude pancreatin which has been obtained in a known manner by suitable precipitation processes from pancreas also to a hydrolytic treatment (autolysis). In this treatment, zymogens are converted into active proteases. This autolytically pretreated pancreatin (abbreviated to F-pancreatin hereinafter) has a particularly high content of active proteases so that these F-pancreatins are at particular risk with regard to their lipolytic activity. The use according to the invention of complex lipids is particularly suitable for stabilizing the lipolytic activity in pharmaceutical preparations containing F-pancreatin. It is surprising in this connection that the stabilization of lipase activity does not take place by inactivation of the active proteases present in the mixture, and the enzyme mixtures stabilized in this way therefore display both amylolytic and lipolytic, and proteolytic activity.

The pancreatin-containing digestive enzyme mixtures in the pharmaceutical preparations to be protected according to the invention may, besides pancreatin, additionally contain those lipases present in plants or microorganisms. Lipases from microorganisms may be those obtained from bacterial or fungus cultures such as molds, for example of the Rhizopus strain.

Additional protease constituents which may be added to pancreatin-containing digestive enzyme mixtures in the pharmaceutical preparations to be protected according to the invention are other animal and plant proteases, and, in particular, proteases which can be obtained from microorganisms such as bacteria or fungus cultures such as molds, for example of the Aspergillus strain.

The lipases which may be present in pancreatin-free digestive enzyme mixtures are those from plants or microorganisms. Lipases from microorganisms may be those obtained from bacteria or fungus cultures such as molds, for example of the Rhizopus strain. Suitable proteases present in pancreatin-free digestive enzyme mixtures are animal or plant proteases, and, in particular, proteases which can be obtained from microorganisms such as bacteria or fungus cultures such as molds, for example of the Aspergillus strain.

Pharmaceutical preparations according to the invention may, besides digestive enzyme mixtures and complex lipids, additionally contain water-soluble pharmaceutical ancillary substances and/or additives. Examples which may be present are vehicles such as carbohydrates, for example mannitol, or soluble proteins, and preservatives.

Pharmaceutical preparations of pancreatin-containing digestive enzyme mixtures for the purpose of the invention may be water-soluble powders which contain, besides pancreatin, in particular F-pancreatin, complex lipids in an amount sufficient to stabilize the lipolytic activity under the influence of moisture, and optionally additionally water-soluble known ancillary substances and/or additives.

Water-soluble powders can be produced by substantially removing constituents which are insoluble in water from the enzyme mixtures. For this purpose, undissolved solids can be removed from an aqueous preparation of F-pancreatin by known methods suitable for removing solids, for example by centrifugation or filtration, and the resulting solutions can, where appropriate after adding other ancillary substances and/or additives, be sterilized by known methods, for example by sterilizing filtration. The ingredients in the resulting clear, optionally sterile solutions can then be obtained as solids again by known drying methods, for example by freeze drying. The preparations obtained in this way are suitable for preparing solutions which are stable for several hours, for example up to 8 hours, and where appropriate are free of microbe growth, and which are suitable for continuous gastrointestinal administration at a constant rate to patients, for example by tube.

Continuous administration means essentially uninterrupted administration of the aqueous solutions which contain the pharmaceutical preparations according to the invention and are, where appropriate, sterile over a period of from about one hour up to several hours, for example 8 hours, for example overnight. Continuous administration of the solutions can advantageously take place through tubes introduced into the digestive tract, for example into the stomach or small intestine.

The efficacy of the added lecithins is substantially independent of the relative lipase/protease ratio in the enzyme mixture. Suitable examples include enzyme mixtures in which the lipase/total protease ratio—measured by the ratio of the respective activities measured in accordance with the provisions of the "Federation Internationale Pharmaceutique" (abbreviated to FIP hereinafter) (see R. Ruyssen and A. Lauwers, Pharmaceutical Enzymes, Scientific Publishing Company, Gent 1978, pages 74–82, quoted as "Lauwers" hereinafter) and indicated hereinafter in relative activity units, abbreviated to FIP-U/g, can be from about 5:1 to about 30:1.

The addition according to the invention of complex lipids to pharmaceutical preparations of digestive enzyme mixtures containing lipases and proteases, in particular pancreatin-containing digestive enzyme mixtures, in principle brings about a stabilization against a decrease in the lipolytic activity under the influence of moisture. Moisture is intended to mean essentially aqueous moisture which may extend from a very low moisture content in the digestive enzyme mixture powder up to an aqueous preparation of this powder.

An addition according to the invention of complex lipids proves to be expedient even during the obtaining and processing of the pancreatin-containing digestive enzyme mixtures used in the pharmaceutical preparations for stabilizing the lipolytic activity during such process steps in the preparation or isolation process in which inactivation of the lipase may occur, such as, for example, a wet treatment of the enzyme mixture.

The stabilizing effect of the added complex lipids, in particular lecithin, in an aqueous solution of a pharmaceutical preparation containing a digestive enzyme mixture also depends, inter alia, on the pH prevailing in the preparation. pH values which have proved beneficial according to the invention are in the pH range of 3.5–9.0, preferably in the range pH 4.0–7.0, particularly preferably in the range pH 5.0–6.5.

To achieve marked stabilization of the lipolytic activity in the water-soluble pharmaceutical preparations of digestive enzyme mixtures and the aqueous solutions which can be prepared from these preparations for administration by tube, it is necessary to add a certain minimum amount of complex lipids. It is normally possible for the digestive enzyme mixtures used in the preparations according to the invention to have a lipase content, expressed in activity units, of, for example, 2000 to 200,000 FIP-U/g when they contain only lipases from mammalian pancreatic secretion, and from 2000 to 500,000 FIP-U/g when they contain lipases from microorganisms either alone or in combination with lipases from pancreas. An amount of at least 1% by weight of complex lipids, based on the amount employed of solid pancreatin-containing digestive enzyme mixture, for example an amount of from 1 to 10% by weight, is then suitable for achieving marked stabilization. Addition of larger amounts of complex lipids is likewise possible but causes no further noticeable improvement in the stabilization of the lipolytic activity. Thus, addition of at least 1% by weight, preferably 2 to 5% by weight, particularly preferably about 3% by weight, of lecithin is suitable, for example, for stabilizing mixtures containing pancreatin, or pancreatin and additional lipase, with complex lipids, in particular lecithin.

It is possible with the aid of the use according to the invention of complex lipids to stabilize such aqueous solutions which can be prepared from pharmaceutical preparations with pancreatin-containing digestive enzyme mixtures and which are prone to a rapid decrease in the lipolytic activity in such a way that the lipolytic activity of the lipases present in the mixture decreases only slightly over a lengthy period. Thus, the aqueous solution of an F-pancreatin stabilized by added lecithin after an incubation time of 8 hours at room temperature shows a remaining lipolytic activity of 85% of the original initial activity. Even after an incubation time of 24 hours, 50% of the initial lipolytic activity was still detectable in an aqueous F-pancreatin solution stabilized by complex lipids. By contrast, the lipolytic activity in a non-stabilized comparison solution had fallen to less than 20% of the initial activity after 8 hours under otherwise identical conditions.

The stabilization according to the invention of water-soluble pharmaceutical preparations of digestive enzyme mixtures containing lipases and proteases against a decrease in lipolytic activity in aqueous medium opens up the possibility of continuously supplying digestive enzyme mixtures of this type in the form of an aqueous solution to patients by introduction into the gastrointestinal tract. The aqueous solutions employed for this purpose should, of course, be free of microbe growth, preferably in fact sterile. Solutions free of microbe growth can be, for example, solutions in which the reproduction of microbes capable of self-reproduction is prevented by addition of preservatives.

There is provision according to the invention of a kit for preparing aqueous solutions, which are suitable for continuous introduction into the gastrointestinal tract by means of a tube, are stabilized against the decrease in lipolytic activity and are free of microbe growth, of digestive enzyme mixtures, characterized in that it contains as components:

a) a water-soluble solid pharmaceutical preparation, which is free of microbe growth, of a digestive enzyme mixture containing lipases and proteases, which may optionally contain an amount of complex lipids which is sufficient for stabilization against a decrease in the lipolytic activity of the aqueous solution to be prepared, and b) an amount, sufficient for preparing the aqueous solution, of an aqueous solvent which is free of microbe growth and which, besides water, may contain physiologically tolerated salts and ancillary substances and, if the solid pharmaceutical preparation mentioned under a) does not contain a sufficient amount of complex lipids for stabilization of the aqueous solution to be prepared against a decrease in the lipolytic activity, additionally contains a sufficient amount of complex lipids for stabilization against a decrease in the lipolytic activity of the aqueous solution to be prepared.

In particular, the solid preparation a) used in the kit can represent a freeze-dried digestive enzyme mixture which contains lipases and proteases and which optionally contains complex lipids. The digestive enzyme mixture is preferably a pancreatin-containing digestive enzyme mixture.

Aqueous solutions which are free of microbe growth can be obtained by adding known preservatives, for example parabens. Sterile solutions which likewise represent solutions free of microbe growth can be obtained by known sterilization methods, for example sterilizing filtration.

The lipids present in the kit can preferably be present as additions already present in the digestive enzyme mixture (component a)). In order to prepare a powder of the digestive enzyme mixtures which already contains the complex lipids, it is possible, for example, for a solution, which is free of microbe growth where appropriate, of the complex lipids to be mixed with a solution, which is free of microbe growth where appropriate, of the digestive enzyme mixture, and subsequently dried by known methods, for example freeze-drying. In order to obtain from this a solution which can be administered by tube, the complex lipids and the powder containing the digestive enzyme mixture must be mixed with the solvent which is likewise present in the kit, where appropriate under conditions with a controlled microbe content or free of microbes. The complex lipids can, however, also be present already dissolved in the solvent (component b)), for example as a colloid. In order to obtain solutions which can be administered by tube, it is necessary in this case to mix the aqueous solution containing complex lipids, or the colloid, where appropriate under sterile conditions, with the digestive enzyme mixture (component a)).

EXAMPLES

1. Stabilization of the Lipolytic Activity of Aqueous Pancreatin Solutions by Soya Lecithin In order to determine the different changes in the lipolytic activity with and without addition of complex lipids in aqueous pancreatin preparations, corresponding samples were prepared and incubated at 30° C. The time-dependent change in the lipase activities in the incubation samples was determined by the method of the "Fédération Internationale Pharmaceutique/European Pharmacopeia" (abbreviated to FIP/Ph.Eur. hereinafter, see Lauwers, pages 74–82). In this standard determination method, the sample to be investigated for lipase activity is allowed to act under hydrolytic conditions on olive oil triglycerides, and the liberated carboxylic acids are titrated against sodium hydroxide to pH 9. The lipase activity of the sample is in this case determined by comparing the rate at which the sample hydrolyses an olive oil emulsion with the rate at which a suspension of a pancreas reference powder hydrolyses the same substrate under the same conditions.

1.1 Investigation of Lipase Stability Without Added Lecithin 79.35 mg of a water-soluble, freeze-dried F-pancreatin with a lipolytic activity of 50473 FIP-U/g were dissolved in 4.0 ml of ice-cold extra-pure water (Nanopur™ supplied by Barnstead), the pH was adjusted to 6.2 with 1 N HCl, and the mixture was subsequently made up to 5.0 ml with extra-pure water. A sample was immediately taken from this mixture to determine the initial lipolytic activity ("time zero sample"). The remaining mixture was incubated in a water bath at 30° C. To take a sample, the mixture was thoroughly mixed, and the sample was removed with a suitable pipette and immediately diluted with ice-cold lipase solvent so that between 0.5 and 1.5 ml of investigation solution with a lipolytic activity of 8 to 16 FIP/U were available for the lipase determination. The lipase solvent used in accordance with FIP/Ph.Eur. was a solution of 10.0 g of NaCl, 6.06 g of tris(hydroxymethyl)aminomethane (abbreviated to "TRIS" hereinafter) and 4.9 g of maleic anhydride in 900 ml of extra-pure water, whose pH was adjusted to pH 7 with 4 N sodium hydroxide solution and which was subsequently made up to 1000 ml with extra-pure water.

In order to measure the time course of the lipase activity, further samples were removed from the thermostatically temperature controlled mixture after 15, 30, 60, 120 and 180 minutes and the lipase activity therein was determined, in each case within 30 minutes, by the FIP/Ph.Eur. method (Lauwers, page 78).

The lipase activity measured in the "time zero sample", in units of FIP-U/ml, was put as 100% value, and the activities measured during the further incubation time are related as percentages to this value. The results are listed in Table 2.

1.2 Investigation of Lipase Stability with Added Lecithin

To prepare a lecithin solution, 100 mg of soya lecithin (phospholipid content about 98% supplied by Roth) were first made into a paste with a little extra-pure water at room temperature and then made up to 20.0 ml. The mixture was irradiated with ultrasound while stirring for about 2 minutes until a homogeneous colloidal solution was obtained. Then 80.0 mg of a water-soluble, freeze-dried F-pancreatin with a lipolytic activity of 54694 FIP-U/gram were dissolved in 4.0 ml of extra-pure water, and the pH in the solution was adjusted to 6.2 with 1 N HCl. 0.4 ml of the lecithin solution (2.5% lecithin based on F-pancreatin powder employed) was added and the mixture was made up, while mixing thoroughly, to 5.0 ml with ice-cold extra-pure water.

The taking of samples and determination of the lipolytic activities at each of the incubation times took place as described under 1.1. The results are listed in Table 2.

TABLE 2

Change in lipolytic activities in aqueous pancreatin solutions with and without added lecithin

| pH | Lecithin added | % lipolytic activity after t [min] | | | | | |
|---|---|---|---|---|---|---|---|
| | | 0 | 15 | 30 | 60 | 120 | 180 |
| 6.2 | — | 100 | 69 | 51 | 41 | 26 | 21 |
| 6.2 | 2.5% | 103 | 93 | 90 | 86 | 80 | 75 |

2. Stabilization of the Lipolytic Activity of Aqueous Pancreatin Preparations over a Period of 8 Hours Losses of lipolytic activity occur in aqueous pancreatin preparations, depending on various factors such as temperature, pH and proteolytic activity of the proteases present. The lipase activity can be distinctly stabilized during incubation at 25° C. for 8 hours by adding complex lipids such as lecithin. Hence, in the following test, the lipolytic activities in aqueous suspensions and solutions of F-pancreatin, in each case with and without addition of complex lipids, were compared over a period of 8 hours.

2.1 Preparation of the Incubation Mixtures

For the comparison, clear pancreatin solutions and pancreatin suspensions from F-pancreatin were in each case investigated with and without added lecithin.

The following aqueous preparations were prepared:

a) Pancreatin Solution Without Lecithin 77.5 mg of a water-soluble, freeze-dried F-pancreatin powder as described under 1.1 were dissolved in ice-cold extra-pure water, adjusting the pH to 6.2 with 1 N HCl.

b) Pancreatin Solution with Lecithin 81.0 mg of a water-soluble, freeze-dried F-pancreatin powder were, after the pH had been adjusted to 6.2, mixed as described under 1.2 with 0.94 ml of lecithin solution and made up to 5.0 ml with ice-cold extra-pure water.

c) Pancreatin Suspension Without Lecithin 2.0 g of F-pancreatin were stirred in 100 ml of ice-cold, extra-pure water for 30 minutes. A cloudy suspension was obtained.

d) Pancreatin Suspension with Lecithin 2.0 g of F-pancreatin were mixed with 100 mg of soya lecithin (supplied by Roth) and stirred in 100 ml of ice-cold extra-pure water for 30 minutes. A cloudy suspension was obtained.

2.2 Test Procedure

Samples were taken immediately after their preparation from the ice-cold solutions and their suspensions prepared as under 2.1 to determine the initial lipolytic activity ("time zero samples"). The remainder of the mixtures was then incubated in test tubes at 25° C. for 8 hours. During this time, further samples were removed after 30 minutes and subsequently each hour. The taking of the samples, dilution and determination of the lipase activity took place as described under 1.1, except that the test temperature was now 25° C.

The lipase activity (indicated in FIP-U/ml) of the "time zero sample" from an incubation mixture was taken as 100% value, and the activities measured during the further incubation time were related as percentages to this value. The results are reproduced in Tables 3 and 4 which follow.

TABLE 3

Course of lipase stability over 8 hours in pancreatin solutions with and without lecithin

| Mixture | % lecithin content | pH | % lipolytic activity after t [h] 0 | 0.5 | 1 | 2 | 3 | 4 | 5 | 6 | 7 | 8 |
|---|---|---|---|---|---|---|---|---|---|---|---|---|
| a) | — | 6.2 | 100 | 72 | 64 | 47 | 36 | 30 | 27 | 24 | 21 | 19 |
| b) | 5.8 | 6.2 | 100 | 97 | 98 | 96 | 98 | 94 | 92 | 89 | 85 | 85 |

TABLE 4

Course of lipase stability over 8 hours in pancreatin suspensions with and without added lecithin

| Mixture | % lecithin content | pH | % lipolytic activity after t [h] 0 | 0.5 | 1 | 2 | 3 | 4 | 5 | 6 | 7 | 8 |
|---|---|---|---|---|---|---|---|---|---|---|---|---|
| c) | — | 7.1 | 100 | 72 | 56 | 43 | 34 | 29 | 25 | 21 | 16 | 16 |
| d) | 5 | 7.1 | 100 | 97 | 97 | 92 | 84 | 77 | 72 | 69 | 64 | 60 |

3. Stabilization of a Microbial Lipase Towards a Microbial Protease by Addition of Complex Lipids The following test showed that the activity of microbial lipases could be stabilized by adding complex lipids even in the presence of active microbial proteases. For this purpose, three investigation solutions containing microbial lipase, microbial lipase plus microbial protease, and microbial lipase with added lecithin plus microbial protease, were prepared. The lipolytic activities in these investigation solutions were then determined and compared with one another in tables.

3.1 Preparation of the Investigation Solutions

The following solutions were prepared:

a) Lipase Solution 245 mg of lipase from *Rhizopus oryzae* (Lipase 7-AP 15, Amano Pharmaceutical Co., LTD Nagoya, Japan) with an activity of 170,000 FIP-U/g were dissolved in 50 ml of ice-cold, 1% strength sodium chloride solution.

b) Protease Solution 390 mg of Aspergillus protease (Prozyme 6; Amano Pharmaceutical Co., LTD Nagoya, Japan) with an activity of 7600 FIP-U/g were dissolved in 25 ml of ice-cold, 1% strength sodium chloride solution.

c) Lecithin Solution 1 g of lecithin (pure soya lecithin phospholipid content about 98%, supplied by Roth) were taken up in 40 ml of extra-pure water ("Nanopure™" supplied by Barnstead) and converted into a colloidal solution with ultrasound while shaking for about 2 minutes.

The following incubation solutions were prepared from these solutions in a total volume of 5 ml in an ice bath:

TABLE 5

Incubation solutions for determining the Rhizopus lipase activity

| Incubation solution | Lipase solution | Protease solution | Lecithin solution | NaCl solution |
|---|---|---|---|---|
| I | 3 ml | — | — | 2 ml |
| II | 3 ml | 1 ml | — | 1 ml |
| III | 3 ml | 1 ml | 1 ml | — |

The pH of all the incubation solutions after preparation was 6.5 at 37° C.

3.2 Test Procedure

Samples were taken immediately after their preparation from the ice-cold incubation solutions I, II and III for determining the initial activities ("time zero samples"), and the remainder of the three mixtures was incubated in test tubes in a water bath at 37° C.

To take a sample, the mixture was thoroughly mixed, and the sample was removed with a suitable pipette and immediately diluted with ice-cold lipase solvent as described under 1.1. Defined amounts were taken from each of these sample solutions (identified by "X" in Table 6) and diluted to 5 ml with 1% strength sodium chloride solution. 0.5 ml of each of these investigation solutions were employed in the lipase activity assay.

TABLE 6

Amounts of sample removed to prepare the investigation solutions

| Investigation solution | X μl of sample solution removed after t = | | |
|---|---|---|---|
| | 0 min | 30 min | 60 min |
| I | 150 | — | 160 |
| II | 160 | 500 | 1000 |
| III | 160 | 250 | 250 |

3.3 Determination of the Rhizopus Lipase Activity

The catalytic activity of Rhizopus lipase was measured by determining the amount of free fatty acids formed from an olive oil emulsion in the presence of 0.025% of sodium taurocholate over a defined period at pH 7.0 and 37° C. In order to ensure that all fatty acids were detected, a titration to pH 9.0 was then carried out. A blank determination by titration of the substrate emulsion served to detect titratable substances not produced by the lipase activity.

The Rhizopus lipase activity of an investigation substance was determined by comparing the rate at which a suspension of the substance hydrolysed an olive oil emulsion with the rate at which a suspension of a Rhizopus lipase reference standard hydrolysed the same olive oil emulsion under the same conditions.

Reagents
1. Water

Extra-pure water "Nanopure™" supplied by Barnstead was used. It is referred to hereinafter simply as "extra-pure water".

2. Gum Arabic Solution 110 g of gum arabic and 12.5 g of calcium chloride were dissolved with stirring (about 3 hours) in extra-pure water, made up to 1000 ml and centrifuged. The solution was dispensed into 250 ml plastic vessels and stored at −20° C.

Gum arabic (acacia gum, DAB 10/Ph.Eur.), calcium chloride analytical grade

3. Substrate Emulsion 130 ml of olive oil and 400 ml of gum arabic solution (2) were emulsified in a suitable stirrer at high speed for 15 minutes. The temperature was kept below 30° C. At least 90% of the droplets in the emulsion had a diameter of less than 3 μm and none was larger than 10 μm. The emulsion was prepared fresh each day. Olive oil (stored in a refrigerator), DAB quality.

4. Sodium Taurocholate Solution 0.5% (m/V)

0.5 g of sodium taurocholate (lipase activating mixture, mixture of conjugated bile acids including sodium taurocholate) was dissolved and made up to 100.0 ml in extra-pure water. The solution was made up freshly each day. Sodium taurocholate (lipase activating mixture), FIP.

5. Sodium Chloride Solution 1% (m/V) in Extra-pure Water

6. Buffer Solution pH 4.5

2 g of sodium chloride and 9.2 g of sodium dihydrogen phosphate were dissolved in about 950 ml of extra-pure water, adjusted to pH 4.5 with hydrochloric acid and made up to 1000 ml with extra-pure water. Sodium chloride analytical grade, sodium dihydrogen phosphate, $NaH_2PO_4 \times H_2O$.

7. Sodium Hydroxide Solution 0.1 N

Reference Suspension

The Rhizopus lipase reference standard was stirred in buffer solution (6) and diluted with sodium chloride solution (5) until the enzyme solution contained 12 to 18 units of Rhizopus lipase activity FIP-U/ml. For a standard with 55,000 FIP-U per 1 g, 63 mg were dissolved in 20 ml of buffer solution (6) in an ice bath over the course of 15 minutes. 10 ml of this solution were diluted with sodium chloride solution (5) to 100 ml in the ice bath. 0.5 ml of this solution were employed in the assay.

Rhizopus lipase reference standard FIP (fungi lipase, FIP standard).

Investigation Solutions

Investigation solutions I, II and III were used.

Test Procedure

The endpoint for the pH-Stat titration was adjusted on the autotitrator of a Radiometer "pH-Stat" titration system to pH 7.0. The following were put in the reaction vessel:

12.0 ml of olive oil emulsion, FIP (3)

6.5 ml of extra-pure water (1)

1.0 ml of sodium taurocholate solution (4)

The mixture was brought to 37.0° C. The pH was adjusted to pH 7.0 with 0.1 N sodium hydroxide solution (7). The burette was then set at "0".

The reaction was started by adding 0.5 ml of reference suspension if the reference value was to be measured, or 0.5 ml of investigation solution if the lipase activity in the investigation solution was to be measured. After 10 minutes, the endpoint for the pH-stat titration was adjusted to pH 9.0. When pH 9.0 was reached, (this step took less than 30 seconds), the titration was stopped and the amount of 0.1N sodium hydroxide solution used was read off.

To determine the blanks, the endpoint of the titration was adjusted to pH 9.0 on the titrator immediately for the reference suspension and the investigation solution. After manual adjustment of the pH in the reaction mixture to pH 7.0 and after addition of 0.5 ml of reference suspension or investigation solution, titration to pH 9.0 was immediately carried out. The Rhizopus lipase activity was calculated in FIP-U/ml of investigation solution from the read-off amount of 0.1 N sodium hydroxide solution used.

The initial lipase activities measured in investigation solutions I, II and III, in units of FIP-U/ml, are put as 100% values. The activities measured during the following incubation time of 1 hour were then each related as percentages to these initial values and listed in Table 7.

TABLE 7

Stabilization of the activity of Rhizopus lipase by soya lecithin

| | | % lipolytic activity after t = | | |
|---|---|---|---|---|
| | Investigation solution | 0 min | 30 min | 60 min |
| I | Lipase solution | 100 | 100 | 95 |
| II | Lipase solution + protease | 100 | 17 | 6 |
| III | Lipase solution with lecithin + protease | 100 | 94 | 84 |

4. Example of a Pharmaceutical Preparation

A) 20.0 g of F-pancreatin are taken up in 400 ml of water, and the pH is rapidly adjusted to 6.2 by adding 1 N HCl. Extraction is carried out under these conditions at 4° C. for 1 hour. The clear supernatant containing the pancreatin extract is centrifuged at 53,000 g and subsequently sterilized by filtration through filters with a pore size of 2 μm.

B) 1.0 g of soya lecithin (98% phosphatidylcholine) are dissolved in 50 ml of water and sterilized in a sealed glass ampoule at 140° C. for 45 minutes.

C) 400 ml of the pancreatin extract prepared in A) are mixed with 25 ml of the lecithin solution prepared in B) under sterile conditions and in the cold. The mixture is freeze-dried, resulting in 16 g of a powder which is dispensed in 2.5 g portions under sterile conditions into 100 ml infusion bottles.

5. Examples of Kits for Pharmaceutical Use 5.1 Kit 1

A) 40.0 g of F-pancreatin are taken up in 400 ml of water, and the pH is rapidly adjusted to 6.2 by adding 1 N HCl. Extraction is carried out under these conditions at 4° C. for 1 hour. The clear supernatant containing the pancreatin extract is centrifuged at 53,000 g and subsequently sterilized by filtration through filters with a pore size of 2 µm. The extract is dispensed in 25 ml portions under sterile conditions into 100 ml infusion bottles and freeze-dried.

B) 2.0 g of soya lecithin (98% phosphatidylcholine) are dissolved in 20 ml of water and homogenized with ultrasound. This colloidal solution is sterilized in a sealed glass ampoule at 140° C. for 45 minutes. A 12.5 ml portion is removed from this, mixed with 1600 ml of sterilized water and dispensed in 100 ml portions into infusion bottles.

For use, the contents of a bottle of the solid obtained in A) are dissolved in the contents of a bottle of the solution obtained in B).

5.2 Kit 2

A) 40.0 g of F-pancreatin are taken up in 800 ml of water, and the pH is rapidly adjusted to 6.2 by adding 1 N HCl. Extraction is carried out under these conditions at 4° C. for 1 hour. The clear supernatant containing the pancreatin extract is centrifuged at 53,000 g, and the precipitate is discarded.

B) 32.0 g of mannitol are dissolved in 200 ml of water and mixed with 800 ml of the pancreatin extract obtained in A), and the combined solutions are sterilized by filtration.

C) 5.0 g of soya lecithin (98% phosphatidylcholine) are dissolved in 50 ml of water and homogenized with ultrasound. This colloidal solution is sterilized in a sealed glass ampoule at 140° C. for 45 minutes.

D) 1000 ml of the pancreatin extract obtained in B) are mixed under sterile conditions with 16 ml of the lecithin solution obtained in C), and freeze-dried. The resulting powder is dispensed in 10.0 g portions into sterile 200 ml bottles.

E) Deionized water which has been sterilized by filtration is dispensed under sterile conditions into 200 ml bottles.

For use, the contents of a bottle of the powder obtained in D) are dissolved in the contents of a bottle of the water dispensed in E).

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents.

What is claimed is:

1. A method of stabilizing a water-soluble pharmaceutical digestive enzyme preparation, comprising:
    preparing an aqueous solution for continuous administration through a tube into the gastrointestinal tract of a patient comprising a lipolytic and proteolytic mixture of digestive enzymes consisting of lipases and proteases; and
    incorporating into said aqueous solution an effective lipolytic activity stabilizing amount of at least one complex lipid comprising lecithin from at least one of a plant source, egg yolk, cerebral matter and microorganisms,
    wherein said stabilizing amount provides an essentially constant lipolytic activity of the digestive enzymes in the aqueous solution throughout a several hour administration period of said aqueous solution.

2. The method according to claim 1, wherein the amount of complex lipid additive comprises at least 1% by weight of the digestive enzyme mixture.

3. The method according to claim 1, wherein the digestive enzyme mixture comprises pancreatin.

4. The method according to claim 3, wherein at least a portion of the complex lipid additive is added to the pancreatin during at least one of isolating the pancreatin from a pancreatin source and processing of the pancreatin prior to incorporating it into the pharmaceutical preparation,
    wherein the pancreatin is stabilized against a decrease in lipolytic activity during process steps associated with wet treatment.

5. The method according to claim 3, wherein the mixture of digestive enzymes comprises pancreatin and at least one lipase selected from the group consisting of plant lipases, bacterial lipases and lipases from fungus cultures.

6. The method according to claim 1, wherein the plant source is selected from the group consisting of soya beans, rapeseed, maize, sunflowers, and peanuts.

7. The method according to claim 6, wherein the plant source is soya beans.

8. The method according to claim 1, wherein said lypolytic and proteolytic mixture further comprises pharmaceutical water-soluble adjuvants.

9. A water-soluble pharmaceutical digestive enzyme preparation suitable for preparing an aqueous solution for continuous administration through a tube into the gastrointestinal tract of a patient, said preparation comprising:
    a lipolytic and proteolytic mixture of digestive enzymes consisting of lipases and proteases; and
    an amount of at least one complex lipid additive comprising lecithin from at least one of a plant source, egg yolk, cerebral matter and microorganisms,
    wherein said amount provides an essentially constant lipolytic activity of the digestive enzymes in an aqueous solution of said pharmaceutical preparation throughout a several hour period.

10. The pharmaceutical preparation according to claim 9, wherein the amount of complex lipid is sufficient to stabilize the lipolytic activity of an aqueous solution of the preparation so that the initial lipolytic activity of the solution decreases by not more than 20% over a period of 8 hours.

11. The pharmaceutical preparation according to claim 10, wherein the amount of complex lipid is sufficient to stabilize the lypolytic activity of the solution so that the initial lipolytic activity of the solution decreases by not more than 50% over a period of 24 hours.

12. The pharmaceutical preparation according to claim 9, wherein the amount of complex lipid comprises from 1 to 10% by weight of the digestive enzyme mixture.

13. The pharmaceutical preparation according to claim 12, wherein the amount of complex lipid comprises from 2 to 5% by weight of the digestive enzyme mixture.

14. The pharmaceutical preparation according to claim 9, wherein the amount of complex lipid additive comprises at least 1% by weight of the digestive enzyme mixture.

15. The pharmaceutical preparation according to claim 9, wherein the plant source is selected from the group consisting of soybeans, rapeseed, maize, sunflowers and peanuts.

16. The pharmaceutical preparation according to claim 9, wherein the lecithin is from microorganisms.

17. The pharmaceutical preparation according claim 9, wherein the lecithin is from chicken eggs.

18. The pharmaceutical preparation according to claim 9, wherein the digestive enzyme mixture comprises pancreatin.

19. The pharmaceutical preparation according to claim 18, wherein the pancreatin comprises autolytically pretreated pancreatin.

20. The pharmaceutical preparation according to claim 18, wherein the proteases from pancreatin are essentially present as pre-activated proteases.

21. The pharmaceutical preparation according to claim 18, wherein the mixture of digestive enzymes comprises pancreatin and at least one lipase selected from the group consisting of plant lipases, bacterial lipases and lipases from fungus cultures.

22. The pharmaceutical preparation according to claim 9, wherein the digestive enzyme mixture comprises lipases from microorganisms selected from the group consisting of bacteria and fungus cultures.

23. The pharmaceutical preparation according to claim 9, wherein the digestive enzyme mixture comprises proteases from microorganisms selected from the group consisting of bacteria and fungus cultures.

24. The pharmaceutical preparation according to claim 9, wherein said water-soluble adjuvants are carbohydrates or proteins.

25. The pharmaceutical preparation according to claim 9, wherein said lypolytic and proteolytic mixture further comprises pharmaceutical water-soluble adjuvants.

26. A kit for preparing an aqueous solution of a digestive enzyme mixture suitable for continuous introduction through a tube into the gastrointestinal tract of a patient, said kit comprising:

a water-soluble, solid pharmaceutical preparation comprising a mixture of digestive enzymes consisting of lipases and proteases and optionally further comprising pharmaceutical water-soluble adjuvants;

an amount of aqueous solvent sufficient for preparing the aqueous solution, said solvent being free of microbe growth; and an amount of at least one complex lipid additive comprising lecithin from at least one of a plant source, egg yolk, cerebral matter and microorganisms contained in at least one of said pharmaceutical preparation and said aqueous solvent, wherein said amount of said complex lipid additive stabilizes the aqueous solution which is to be prepared throughout a several hour period.

27. The kit according to claim 26, wherein said aqueous solvent further comprises physiologically acceptable salts and ancillary substances.

28. The kit according to claim 26, wherein the complex lipid additive is contained in the solid pharmaceutical preparation.

29. The kit according to claim 26, wherein the complex lipid is contained in the aqueous solvent.

30. The kit according to claim 26, wherein part of the complex lipid is contained in the solid pharmaceutical preparation and the remainder is contained in the aqueous solvent.

31. The kit according to claim 26, wherein the solid pharmaceutical preparation is a freeze-dried mixture of digestive enzymes selected from lipases and proteases.

32. The kit according to claim 31, wherein the freeze-dried mixture further comprises an effective lypolytic activity stabilizing amount of at least one complex lipid additive.

33. The kit according to claim 31, wherein the freeze-dried enzyme mixture comprises pancreatin.

* * * * *